(12) United States Patent
Hu et al.

(10) Patent No.: US 11,795,200 B2
(45) Date of Patent: Oct. 24, 2023

(54) NANO SMALL PEPTIDE AND ITS USE IN PREPARATION OF DRUGS FOR TREATING AND PREVENTING FUNDUS VASCULAR DISEASES

(71) Applicant: FUTU Biotech Co., Ltd., Wuhan (CN)

(72) Inventors: Bo Hu, Wuhan (CN); Yanan Li, Wuhan (CN); Hao Wang, Beijing (CN); Lei Wang, Beijing (CN)

(73) Assignee: FUTU Biotech Co., Ltd., Wuhan (CN)

( * ) Notice: Subject to any disclaimer, the term of this patent is extended or adjusted under 35 U.S.C. 154(b) by 0 days.

(21) Appl. No.: 17/898,470

(22) Filed: Aug. 29, 2022

(65) Prior Publication Data

US 2023/0102129 A1 Mar. 30, 2023

(30) Foreign Application Priority Data

Aug. 29, 2021 (CN) .......................... 202110999538.8

(51) Int. Cl.
  *C07K 7/08* (2006.01)
  *A61K 47/54* (2017.01)
  *A61P 9/14* (2006.01)
  *A61K 38/00* (2006.01)

(52) U.S. Cl.
  CPC .............. *C07K 7/08* (2013.01); *A61K 47/543* (2017.08); *A61P 9/14* (2018.01); *A61K 38/00* (2013.01)

(58) Field of Classification Search
  CPC ........ C07K 7/08; A61K 47/543; A61K 38/00; A61P 9/14
  See application file for complete search history.

(56) References Cited

PUBLICATIONS

Zhang et al, An antibody-like peptidic network for anti-angiogenesis, Biomaterials, 2021, 275, pp. 1-10.*
Bo Hu et al., co-pending U.S. Appl. No. 17/898,331, filed Aug. 29, 2022, titled "Nano Small Peptide and its Use in Preparation of Drugs for Treating and Preventing Fundus Vascular Diseases."

* cited by examiner

*Primary Examiner* — Li N Komatsu
(74) *Attorney, Agent, or Firm* — MEI & MARK LLP; Manni Li

(57) ABSTRACT

A nano small peptide FG and its use in preparation of drugs for treating and preventing fundus vascular diseases are provided. The artificially synthesized nano small peptide has a molecular formula of X-FFVLKKNKAAKG (SEQ ID NO:1), wherein the X is dodecanoyl, tetradecanoyl, hexadecanoyl, or octadecanoyl group. The nano small peptide of the present invention can specifically select receptors to encapsulate sSema4D protein, and the concentration of sSema4D is effectively reduced, so that the sSema4D is unable to bind to any receptors, thus changing the shortcoming of few inhibitory targets of antibody drugs. The nano small peptide molecule with a simple structure can be mixed with antibody drugs without causing mutual immune reactions, so as to achieve the effect of reducing multiple pro-angiogenesis molecules.

7 Claims, 9 Drawing Sheets

Figure 1A:
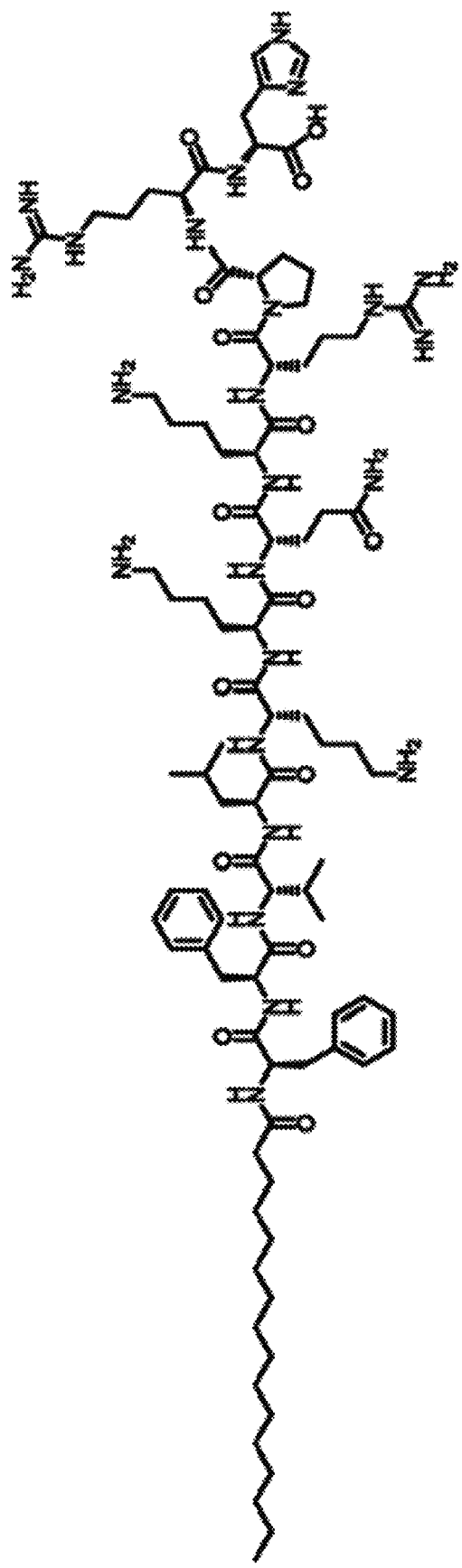
Figure 1B:
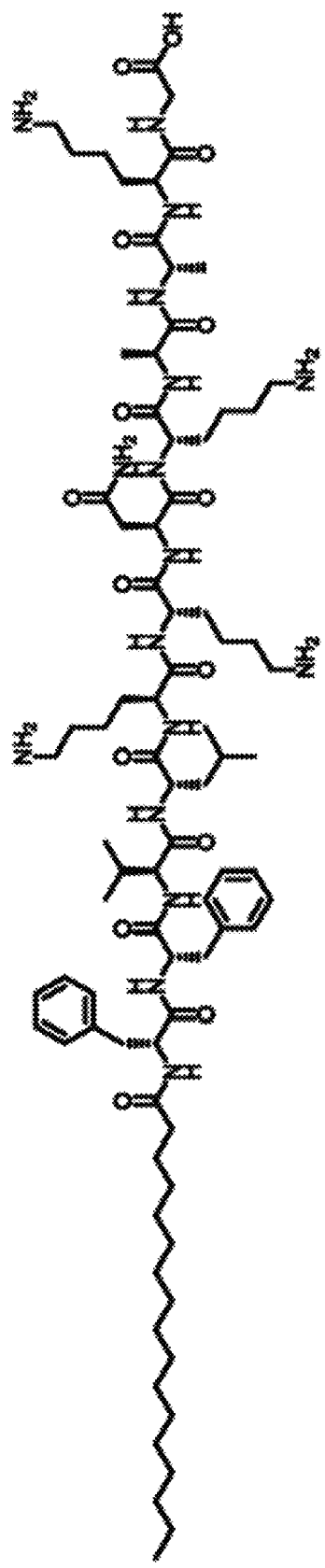

Specification includes a Sequence Listing.

FH: hexadecanoyl-FFVLKKQKRPRH (SEQ ID NO: 2)

M.W.: 1822.38

FG: hexadecanoyl-FFVLKKNKAAKG (SEQ ID NO: 1)

M.W.: 1589.10

NANO SMALL PEPTIDE AND ITS USE IN PREPARATION OF DRUGS FOR TREATING AND PREVENTING FUNDUS VASCULAR DISEASES

CROSS-REFERENCE TO RELATED APPLICATIONS

The subject application claims priority on Chinese patent application no. 202110999538.8 filed on Aug. 29, 2021 in China. The contents and subject matters of the Chinese priority application is incorporated herein by reference.

REFERENCE TO AN ELECTRONIC SEQUENCE LISTING

The contents of the electronic sequence listing (Name of the File: ReplacementSequenceListing8024wh.xml; Size: 4k bytes; and Date of Creation: Jul. 1, 2023) is herein incorporated by reference in its entirety.

BACKGROUND OF THE INVENTION

Technical Field

The present invention belongs to the field of biomedicine, and in particular relates to a nano small peptide (hereinafter referred to as FG) and its use in preparation of drugs for treating and preventing fundus vascular diseases.

Description of Related Art

Diabetic retinopathy (DR) is the most common and most serious complication of diabetes. The main pathological changes of DR are excessive retinal angiogenesis and vascular leakage and their core mechanism is that local hypoxia induces the "excessive" release of pro-angiogenic factors, causing a large accumulation of pro-angiogenic factors in the vitreous humor and inducing "excessive" new blood vessels; however, the walls of these new blood vessels are incomplete and increase leakage, leading to macular edema, retinal detachment and blindness. In view of the above mechanism, there are mainly three types of treatments available for DR at present: (1) laser photocoagulation treatment; (2) vitrectomy; (3) intravitreal injection of anti-angiogenic drugs, among which, the laser photocoagulation treatment is a treatment method like the trick of giving up a rook to save the king in chess, in which peripheral vision is sacrificed to save central vision, and the method has been gradually replaced by the intravitreal injection of anti-angiogenic drugs. Since VEGF-A (vascular endothelial growth factor A) plays an important role in angiogenesis and leakage, intravitreal injection of anti-VEGF drugs has been widely used in the clinical treatment of diabetic macular edema and proliferative diabetic retinopathy. Although the anti-VEGF treatment offers many benefits to clinical patients, there are following bottlenecks about the anti-VEGF treatment:

1. Low effective rate of the anti-VEGF treatment: the anti-VEGF treatment is effective only for 30% of patients receiving the anti-VEGF treatment, these patients have poor response to anti-VEGF treatment, and despite frequent injection of anti-VEG drugs alone, there will still be persistent macular edema.

2. Serious potential harm: (1) infection, cataract formation, and vitreous hemorrhage complicated by repeated injections and administration may aggravate the disease and lead to retinal detachment and blindness more quickly; and (2) VEGF has a protective effect on neurons and reduces the concentration of VEGF. The neurotoxicity produced due to lowering VEGF levels too low can lead to retinal atrophy, thereby aggravating vision loss.

3. High requirements for injection technology: the anti-VEGF treatment requires vitreous injection, which is an invasive treatment method. Some patients need to be operated under the microscope, which is difficult to carry out and popularize in primary hospitals. However, there are many DR patients; so many patients are unable to receive effective treatment;

4. Expensive antibody drugs: since the anti-VEGF treatment is only temporarily effective for macular edema patients, monthly injections or even more frequent injections are required to control edema, and the treatment for several years cannot be afforded by ordinary families, bringing a heavy economic burden to the families and society.

5. Few corresponding inhibitory targets of the anti-VEGF treatment: the VEGF family includes VEGF121, 165, 181, and the like which have multiple binding targets with different antibodies existing in different cells. However, during preparation of anti-VEGF drugs, relatively most effective binding sites are selected while ignoring other binding sites, resulting in that VEGF can play an effective role through other binding sites in some patients. This may be one of the reasons why the effectiveness of anti-VEGF treatment is only 30%, which is not only a limitation of anti-VEGF drugs, but also a common defect of antibody drugs.

6. sSema4D plays a crucial role in promoting angiogenesis and vascular leakage as follows. The applicant performed protein chip analysis on 114 diabetic retinopathy (DR) aqueous humor samples and screened out 275 proteins, and it was found that the 140KD Sema4D fragment was specifically highly expressed, and the higher the concentration of sSema4D in the aqueous humor, the less effective the anti-VEGF treatment. It was also found that: (1) In the Sema4D knockout mouse model of retinal neovascularization (OIR model), the pathological angiogenesis was significantly reduced, and the vascular leakage was significantly reduced in the streptozotocin-induced diabetic mouse model (STZ model). (2) The synergistic effect of single injection of anti-Sema4D drug and anti-VEGF drug was significantly better than that of the simple anti-VEGF treatment. (3) Multiple injections of anti-Sema4D drug were superior to the anti-VEGF treatment in reducing vascular leakage. The above results validate the superiority of anti-Sema4D treatment over the anti-VEGF treatment. That is to say, reducing the concentration of sSema4D is an effective therapeutic target to inhibit fundus angiogenesis and vascular leakage. However, the current clinical dilemma is that using multiple receptor antagonists may stimulate mutual immune mechanisms, resulting in poor efficacy or increased side effects.

BRIEF SUMMARY OF THE INVENTION

An objective of the present invention is to provide an artificially synthesized nano small peptide having a molecular formula of X-FFVLKKNKAAKG (SEQ ID NO:1), wherein the X is dodecanoyl, tetradecanoyl, hexadecanoyl, or octadecanoyl group.

Another objective of the present invention is to provide use of an artificially synthesized nano small peptide in the preparation of drugs for treating and preventing ocular fundus vascular diseases.

In order to achieve the above objectives, the present invention adopts the following technical solution.

Provided is an artificially synthesized nano small peptide, having a molecular formula of X-FFVLKKNKAAKG (SEQ ID NO: 1), wherein the X is dodecanoyl, tetradecanoyl, hexadecanoyl, or octadecanoyl group; when the X is hexadecanoyl, the structural formula is:

FG: hexadecanoyl-FFVLKKNKAAKG (SEQ ID NO:1)

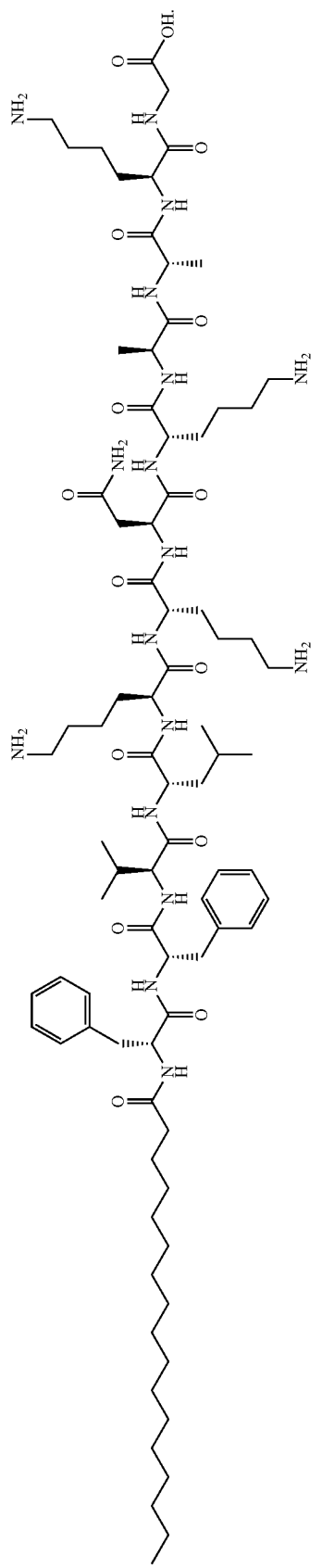
M.W.: 1589.10

Provided is use of the above-mentioned artificially synthesized nano small peptide in preparation of drugs for treating and preventing fundus vascular diseases, The fundus vascular diseases include but are not limited to: diseases caused by fundus angiogenesis, diseases caused by fundus pathological vascular leakage, disease due to pericyte migration, and disease due to endothelial cell migration or leakage.

In the above use, the dosage forms of the drugs include all pharmaceutically acceptable dosage forms, including but not limited to tablets, capsules, granules, injections, powders, drops, or the like.

Compared with the prior art, the present invention has the following advantages:

1. The nano small peptide of the present invention can be administered in the form of eye drops: it is a non-invasive, safe, effective and easy-to-operate way, breaking through the technical bottleneck that current clinical drugs must be invasively and repeatedly injected into the vitreous body.

2. The nano small peptide of the present invention can specifically select receptors to encapsulate the sSema4D protein, and the concentration of sSema4D is effectively reduced, so that the sSema4D is unable to bind to any receptors, thus changing the shortcoming of few inhibitory targets of antibody drugs.

3. The nano small peptide molecule (FG) is a non-protein product with a simple structure and can be mixed with antibody drugs without causing mutual immune reactions, so as to achieve the effect of reducing multiple pro-angiogenesis molecules.

4. The nano small peptide molecule (FG) is one percent of the mass of the antibody drugs currently used in clinic, and it also has significant advantages in quality. With 1 small molecular weight, it can be instilled in the eyes. The peptide itself is different.

5. The action time of the nano small peptide molecule (FG) is significantly better than that of antibody drugs, which reduces the number of patients' medication and breaks through the bottleneck of clinical treatment.

6. The nano small peptide molecule (FG) is easy to prepare, and the preparation cost is low, which can greatly reduce the treatment cost. And the relevant mechanisms are clarified.

BRIEF DESCRIPTION OF THE SEVERAL VIEWS OF THE DRAWINGS

FIGS. 1A and 1B show the molecular structures of nano small peptides FH as in FIG. 1A and FG as in FIG. 1B.

FIGS. 2A to 2C show partial physicochemical properties of the nano small peptides FH and FG including CD spectra and dynamic light scattering (DLS) spectra of FH and FG nanoparticles, wherein FIG. 2A shows the CD spectrum of FH (vertical axis represents the Number (Percent)); FIG. 2B shows the DLS spectrum (vertical axis in scales show the Particle (d.nm) on the left and Zeta potential (mV) on the right), and FIG. 2C shows the CD spectrum of FG (vertical axis represents the Number (Percent)).

FIGS. 3A and 3B show that the nano small peptides FH and FG can sustainably reduce the concentration of sSema4D, which is significantly better than that of antibody drugs in terms of duration, where FIG. 3A shows that nano small peptides FH and FG can sustainably reduce the concentration of sSema4D in a simple medium system, which is significantly better than that of antibody drugs in terms of duration; and FIG. 3B shows that the addition of nano small peptides FH and FG to endothelial cells can sustainably reduce the concentration of sSema4D, which is significantly better than that of antibody drugs in terms of duration. The vertical axis represents sSema4D concentration (ng/ml) in both figures.

FIGS. 4A and 4B show that nano small peptides FH and FG can significantly inhibit fundus angiogenesis in an OIR model, where FIG. 4A shows the results of immunofluorescence staining, indicating that the nano small peptides FH and FG can significantly inhibit the pathological angiogenesis of the fundus, and FIG. 4B shows the results of immunofluorescence staining, indicating that nano small peptides FH and FG can significantly inhibit the pathological angiogenesis of the fundus. The vertical axis in FIG. 4B represents Neovascularization.

FIGS. 5A and 5B show that nano small peptides FH and FG can significantly inhibit the leakage of fundus blood vessels in an STZ model, where FIG. 5A shows the results of the Evans blue leakage test, indicating that the nano small peptides FH and FG can significantly inhibit the pathological vascular leakage of the fundus, and FIG. 5B is a statistical diagram of the results of the Evans blue leakage test, indicating that nano small peptides FH and FG can significantly inhibit the pathological vascular leakage of the fundus. The vertical axis in FIG. 5B represents the Evans blue value (fold change).

FIGS. 6A, 6B, and 6C show that the nano small peptides FH and FG significantly inhibiting endothelial cell migration and leakage, where FIG. 6A to 6B show the results of transwell experiments and scratch experiments, confirming that nano small peptides FH and FG can block sSema4D from promoting endothelial cell migration (the vertical axis in FIG. 6B represents Migrated cells (fold change)); and FIG. 6C shows the results of TEER and fluorescein leakage experiments, confirming that nano small peptides FH and FG can block sSema4D from promoting endothelial cell leakage (the vertical axis in FIG. 6C shows fold change).

FIGS. 7A and 7B show the nano small peptide FH significantly inhibiting pericyte migration, where FIG. 7A shows the results of transwell experiments, confirming that nano small peptides FH and FG can block sSema4D from promoting pericyte migration, and FIG. 7B is a statistical diagram of the results of transwell experiments, confirming that nano small peptides FH and FG can block sSema4D from promoting pericyte migration. The vertical axis in FIG. 7B represents Migrated cells.

FIGS. 8A and 8B show that the nano small peptide FH can enter the vitreous humor and reduce the concentration of sSema4D in the form of eye drops, where FIG. 8A shows the tests of in vivo imaging of small animals, confirming that nano small peptides FH and FG enter the vitreous humor of mice in the form of eye drops, and FIG. 8B shows the results of Elisa tests, showing that FH and FG eye drops can reduce the concentration of sSema4D in vitreous humor. The vertical axis in FIG. 8B represents sSema4D concentration (ng/ml).

DETAILED DESCRIPTION OF THE INVENTION

The present invention will be described further with reference to specific embodiments. The technical solutions of the present invention, unless otherwise specified, are conventional solutions in the field. The reagents or materials, unless otherwise specified, were obtained from commercial sources. The sSema4D protein of the present invention is the free Sema4D protein after enzyme cleavage of Sema4D, that is, the sSema4D protein purchased from R&D Systems Company. In the embodiment of the present invention, the hexadecanoyl group in the FH sequence can also be replaced with octadecanoyl, tetradecanoyl, or dodecanoyl group. The present invention takes hexadecanoyl group as an example to describe its effect. Because of limited space, the technical effect of the present invention can still be obtained by replacing it with carbon chains of other lengths mentioned above.

In the embodiment of the present invention, the hexadecanoyl group in the FG sequence can also be replaced with octadecanoyl, tetradecanoyl, or dodecanoyl group. The present invention takes the hexadecanoyl group as an example to describe its effect. Because of limited space, the technical effect of the present invention can still be obtained by replacing it with carbon chains of other lengths mentioned above.

Example 1

The nano small peptides FH (SEQ ID NO: 2) and FG (SEQ ID NO:1), X being hexadecanoyl, having the following molecular structures, can be directly synthesized commercially:

solution A was quickly added to 1 mL of water, and the resulting solution was then vortexed for 30 s to obtain a nanoparticle solution. Second, samples were made. 10 ul of FG (or FH) solution was added dropwise onto a copper mesh for 5 min, and the excess solution was removed with filter paper. 10 μL of uranyl acetate stain was added dropwise for 5 min, and the excess stain was removed with filter paper. Washing with 10 μl of deionized water was carried out once. The samples were dried in vacuum overnight. Finally, transmission electron microscopy observations were performed on an HT-7700 transmission electron microscope (Hitachi, Tokyo, Japan). Scale bar was 200 nm.

CD spectra of FH and FG nanoparticles:

The CD spectra of FH and FG nanoparticles (20 μM) were collected at room temperature using a CD spectrometer (JASCO-1500, Tokyo, Japan) with an optical path length of 1 mm. Measurements were performed between 190 nm and 300 nm with a resolution of 1.0 nm at a scan speed of 300 nm/min. For each measurement, three spectra were collected and averaged.

Figure 2C:
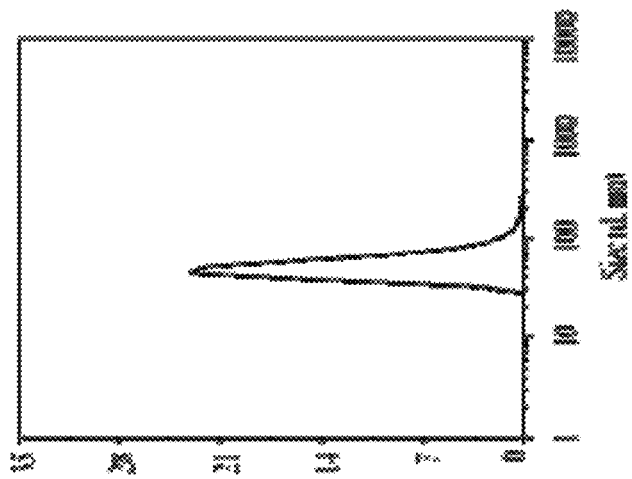
Figure 2B:
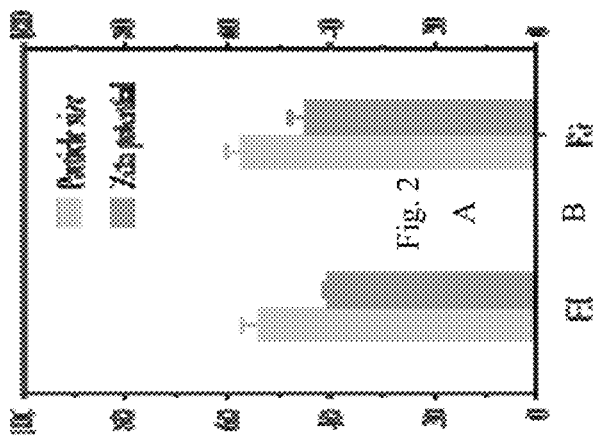
Figure 2A:
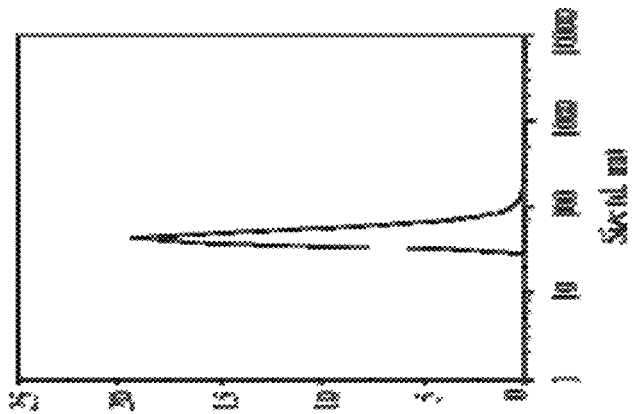

The results are shown in FIGS. 2A to 2C. CD spectroscopy measurement shows that the signal at 200 nm is

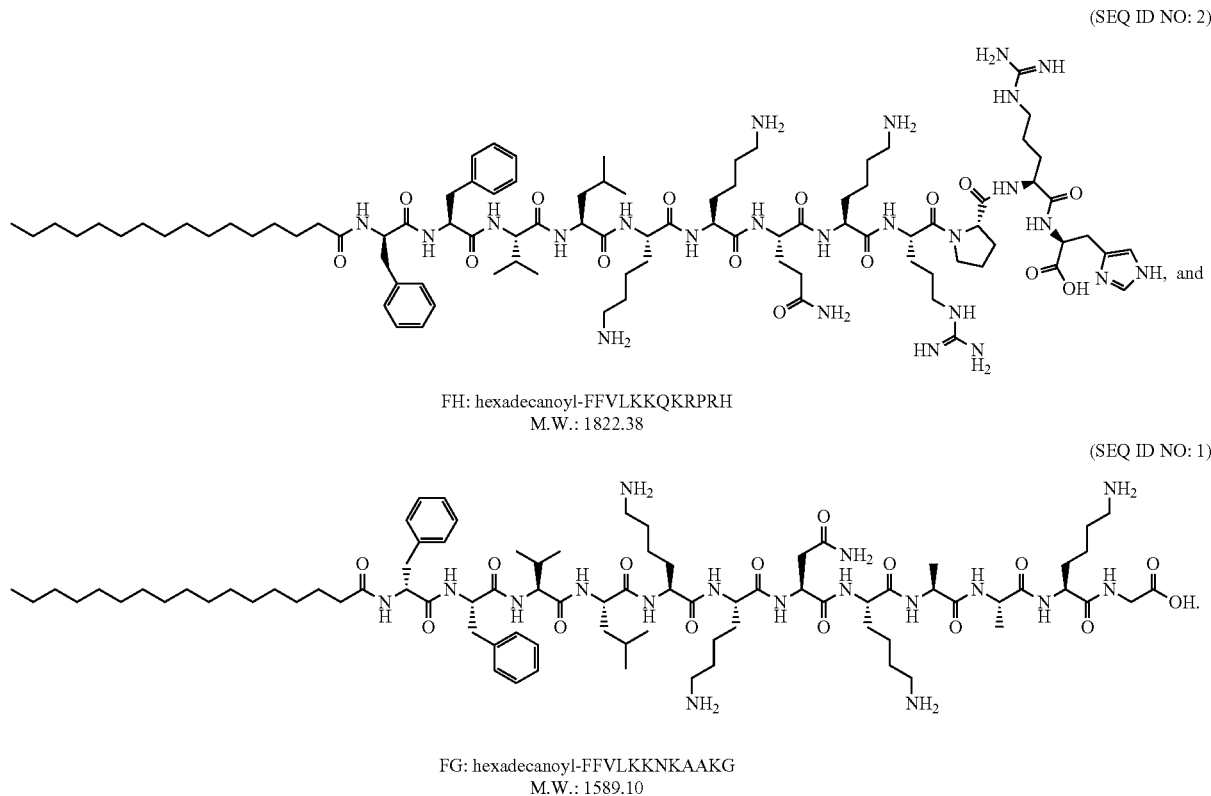

FH: hexadecanoyl-FFVLKKQKRPRH
M.W.: 1822.38

FG: hexadecanoyl-FFVLKKNKAAKG
M.W.: 1589.10

Example 2

Characterization and Cytotoxicity of Nanoparticles FH and FG

First, FG and FH nanoparticle solutions with a concentration of 20 μM were prepared as follows. 0.01 mmol of FG (or FH) was weighed and dissolved in 1 mL of DMSO solution, and then diluted into 5 folds to a concentration of 2 mM, thus obtaining mother solution A. 10 μL of mother negative before FH and FG nanoparticles (20 μM, $H_2O$ containing 0.5% of dimethyl sulfoxide) are induced by sSema4D protein, indicating a random coil structure; the signal at 200 nm is positive and accompanied by a negative signal at 220 nm after induction by the addition of sSema4D protein, indicating a transition to a (3-sheet folded structure.

DLS Spectra of FH and FG Nanoparticles

The particle size and zeta potential of FH and FG nanoparticles were measured with a zeta sizer (Nano ZZ90, Malvern, UK) at 25° C.

The results are shown in FIGS. 2A to 2C. The particle diameters of the FH and FG nanoparticles are 54.43±2.8 nm and 57.67±2.6 nm, respectively. The charges of the FH and FG nanoparticles are +40.4 mV and +44.8 mV, respectively.

Using CCK8 assay, it was found that 20 μM nano small peptides FH and FG did not cause toxic effects on endothelial cells (primary endothelial cells of mouse brain microvessels) at 12, 14, and 36 h.

Example 3

The nano small peptides FH and FG can sustainably reduce the concentration of sSema4D, which is significantly better than that of antibody drugs in terms of duration.

1) The nano small peptides FH and FG can sustainably reduce the concentration of sSema4D in a simple medium system, which is significantly better than that of antibody drugs in terms of duration.

The nano small peptides FH, FG, DMSO, and Sema4D neutralizing antibody (BMA-12) were added to the medium (the concentration of sSema4D in the medium was 1600 ng/mL) to ensure that the final concentration of FH and FG was 20 μM, and the final concentration of the Sema4D neutralizing antibody (BMA-12) (BMA-12, i.e., anti-Sema4D) was 2 μg/μL, an equal volume of DMSO was then added as a control, and culture plates were set still at 37° C. for 12, 24, 36, and 48 h, and the culture medium was collected, and the expression of Sema4D protein in the supernatant was detected using an ELISA kit (Shanghai Yuanmu Biotechnology Co., Ltd.).

Figure 3A:
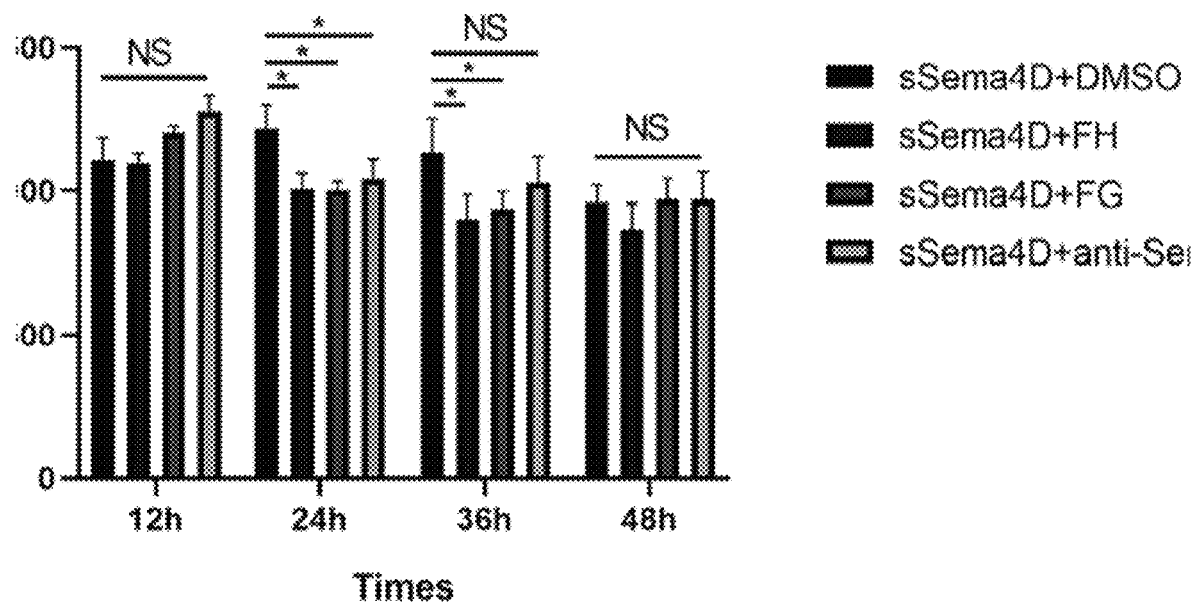

The results are shown in FIG. 3A. The results show that all the FH, FG, and Sema4D neutralizing antibody (BMA-12) can reduce the sSema4D concentration at 24 h; at 36 h, the FH and FG can still reduce the sSema4D concentration, while the anti-Sema4D fails to reduce the sSema4D concentration, and within the same action time, the effect of FH is better than that of FG.

2) The addition of nano small peptides FH and FG to endothelial cells (mouse brain microvascular primary endothelial cells) can sustainably reduce the concentration of sSema4D, which is significantly better than antibody drugs in terms of duration.

Endothelial cells were uniformly seeded in 6-well cell culture plates and cultured in a 5% CO2 incubator at 37° C. for 24 h. The nano small peptides FH, FG, DMSO, and Sema4D neutralizing antibody (BMA-12) were added to the medium (the concentration of sSema4D in the medium was 1600 ng/mL) to ensure that the final concentration of FH and FG was 20 μM, and the final concentration of the sSema4D neutralizing antibody (BMA-12) was 2 μg/μL, an equal volume of DMSO was then added as a control, and the culture plates were cultured in an incubator for 12, 24, 36, and 48 h, respectively. The cell culture medium was then collected and centrifuged. The supernatant was taken and the expression of Sema4D protein in the supernatant was detected using an ELISA kit (Shanghai Yuanmu Biotechnology Co., Ltd.).

Figure 3B:
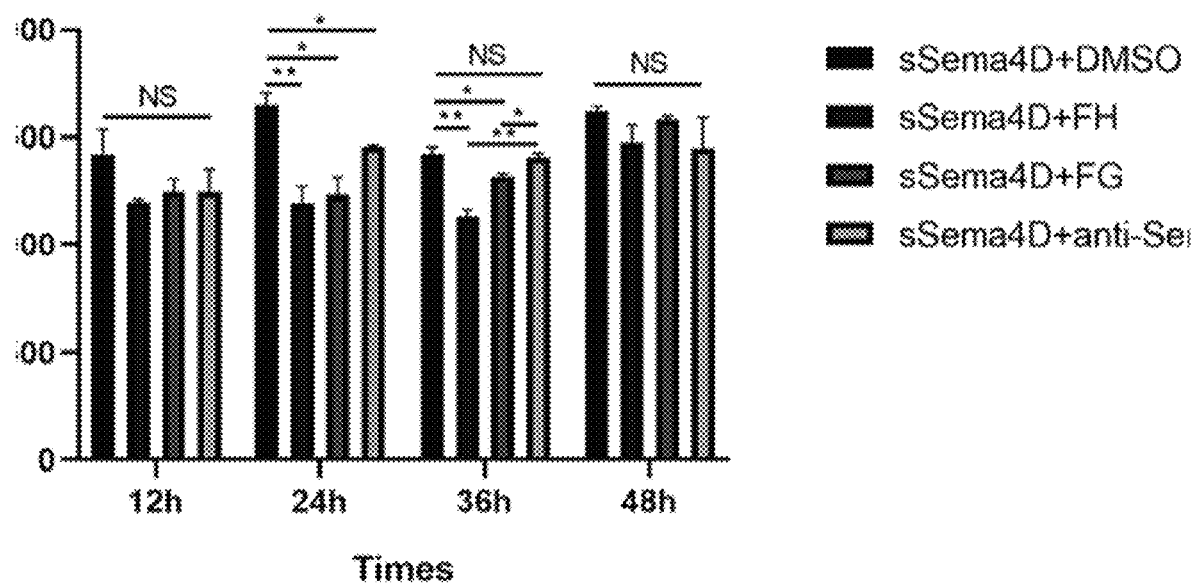

The results are shown in FIG. 3B. The results show that both the FH and BMA-12 neutralizing antibody (BMA-12) can reduce the sSema4D concentration at 24 h; at 36 h, the FH can still reduce the sSema4D concentration, while the BMA-12 neutralizing antibody (BMA-12) fails to reduce the sSema4D concentration, and within the same action time, the effect of FH is better than that of FG.

Example 4

Confocal detection shows that the nano small peptides FH and FG can significantly inhibit fundus angiogenesis in an OIR model.

Treatment group (OIR): After giving birth, 3-4 month old C57BL/6 mother mice were placed in an oxygen chamber with 75% oxygen together with 7 day old young mice, and the young mice and the mother mice were taken out on the 12th day of birth of the young mice. Immediately after the young mice were anesthetized, 2 nmol of FH, 2 nmol of FG, and 1 μg of Sema4D neutralizing antibody (BMA-12) (BMA-12, i.e., anti-Sema4D) were injected into the vitreous, and an equal volume of DMSO was used as a control. The young mice were then further raised in normal air for 5 days; the young mice were anesthetized on the 17th day of birth, and after cardiac perfusion with normal saline, the eyeballs were separated and then fixed, stained with Isolectin B4 overnight at 4° C., flatly spread on a glass slide, and photographed.

Figure 4A:
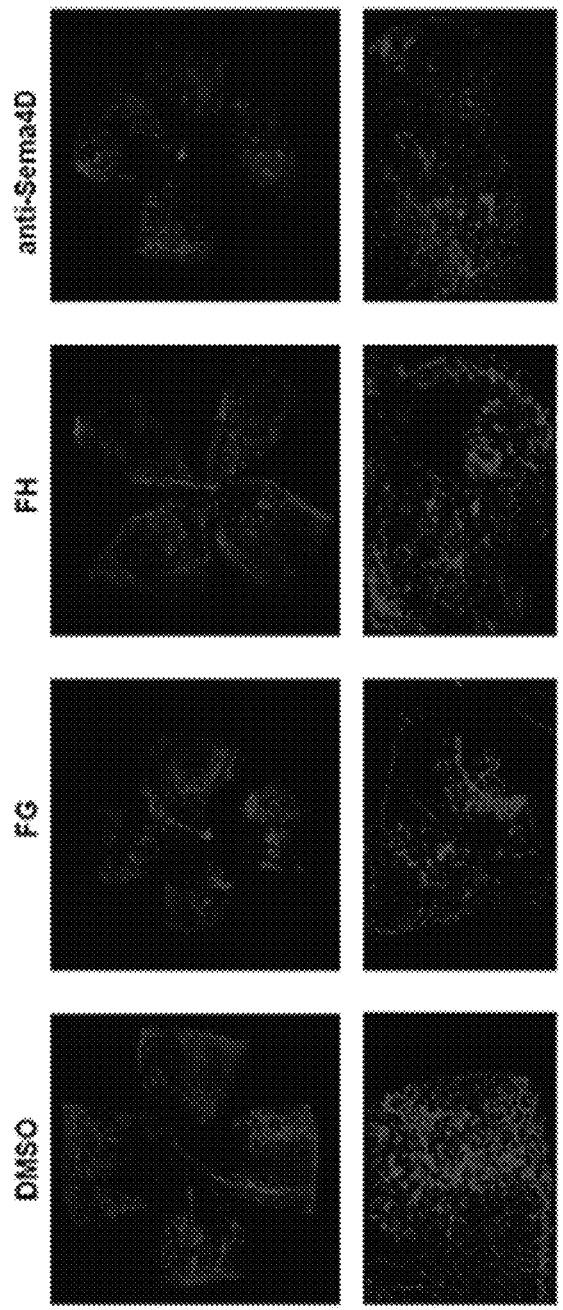
Figure 4B:
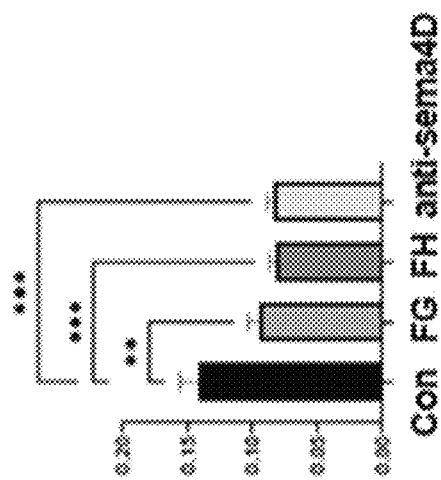

Control group (Normal): Young mice, grown with normoxia, were anesthetized on the 17th day of birth. After cardiac perfusion with normal saline, the eyeballs were taken out, and the retinas were peeled off and then fixed with 4% paraformaldehyde, stained with Isolectin B4 at 4° C. overnight, flatly spread on a glass slide, and photographed The results are shown in FIG. 4A. Laser confocal was carried out to detect retinal angiogenesis, and ImageJ was carried out to calculate the ratio of retinal neovascularization clusters to the entire retinal area, that is, the proportion of new blood vessels. The results show that FH and FG reduce the percentage of abnormal blood vessels in the total retinal area, indicating that FH and FG treatment can inhibit the angiogenesis of the fundus in the OIR model mice, and their treatment effect is comparable to that of the Sema4D neutralizing antibody (BMA-12). It can be seen in FIG. 4A that the treatment effect of FH is the best.

Example 5

The Evans blue leakage test shows that the nano small peptides FH and FG can significantly inhibit the vascular leakage of the fundus in the OIR model mice.

Figure 5A:
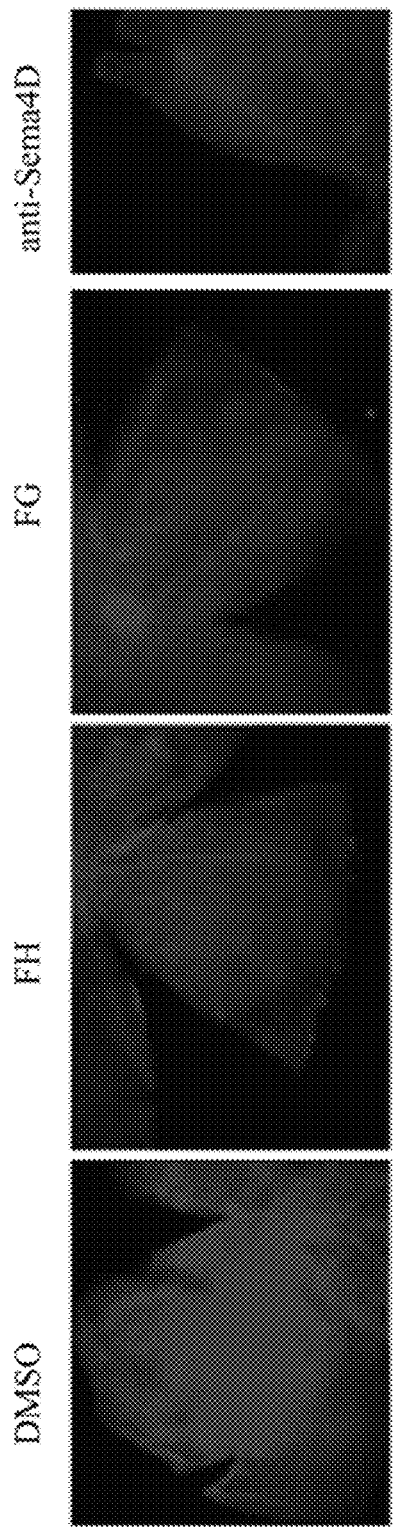
Figure 5B:
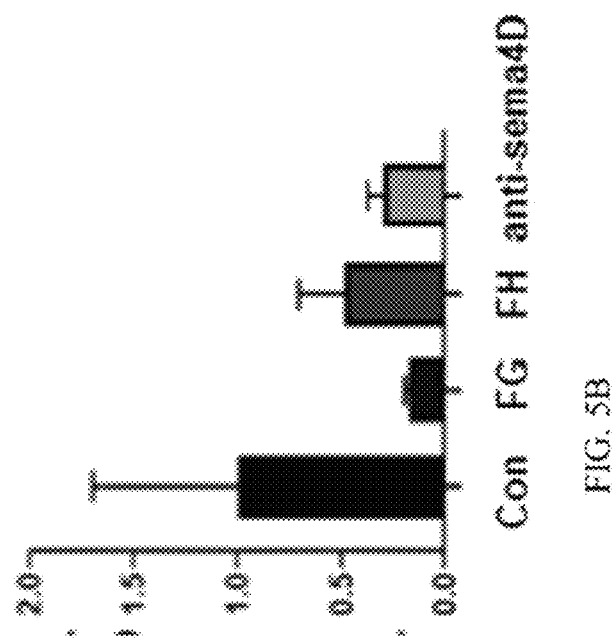

Treatment group (OIR): After giving birth, 3-4 month old C57BL/6 mother mice were placed in an oxygen chamber with 75% oxygen together with 7 day old young mice, and the young mice and the mother mice were taken out on the 12th day of birth of the young mice. Immediately after the young mice were anesthetized, 2 nmol of FH, 2 nmol of FG, and 1μg of Sema4D neutralizing antibody (BMA-12) were injected into the vitreous, and an equal volume of DMSO was used as a control. The young mice were then further raised in normal air for 5 days; the young mice were anesthetized on the 17th day of birth, and after cardiac perfusion with normal saline, the eyeballs were separated and then fixed, stained with Isolectin B4 overnight at 4° C., flatly spread on a glass slide, and photographed Control group (Normal): Young mice, grown with normoxia, were anesthetized on the 17th day of birth. After cardiac perfusion with normal saline, the eyeballs were taken out, and the retinas were peeled off and then fixed with 4% paraformaldehyde, ruptured with 3% triton, blocked with 15% donkey serum, stained with Isolectin B4 overnight at 4° C., flatly spread on a glass slide, and photographed with a fluorescence microscope The results are shown in FIGS. 5A and 5B. The results show that FH and FG reduce the percentage of abnormal blood vessels in the total retinal area, indicating that FH and FG treatment can inhibit vascular leakage of the fundus in the OIR model mice, and their treatment effect is comparable to that of anti-Sema4D.

Example 6

The nano small peptides FH and FG significantly inhibit endothelial cell migration and leakage.

1) The nano small peptide FH significantly inhibits endothelial cell migration (transwell experiment)

The primary mouse brain microvascular endothelial cells were starved with 0.5% ECM for 4 to 6 h. The mouse brain microvascular endothelial cells were seeded in the upper layer of a 24-well transwell chamber (8 µM). 1% ECM medium containing FH (20 µM), FG (20 µM), and Sema4D neutralizing antibody (BMA-12) (2 µg/µL) (the concentration of sSema4D in the medium is 1600 ng/mL) was added to the lower chamber, and an equal volume of DMSO was added as control. The cells were incubated in a 5% CO2 incubator at 37° C. for 24 h. 24 h later, the cells on the bottom of the chamber were fixed with 4% paraformaldehyde and stained with crystal violet, and the endothelial cells that penetrated to the bottom of the chamber were counted under a microscope.

Figure 6A:
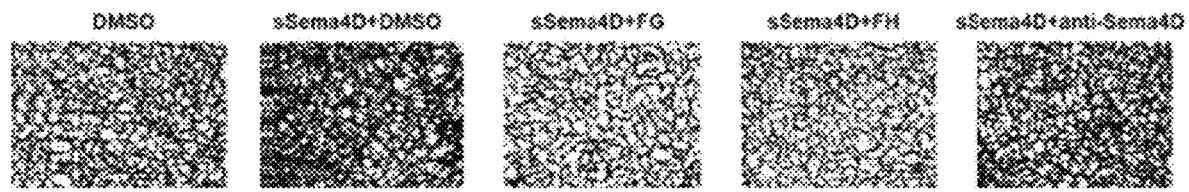
Figure 6B:
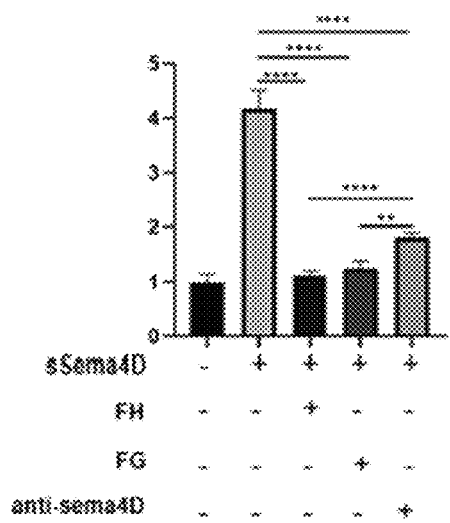

The results are shown in FIGS. 6A and 6B: At 24 h, FH and FG can significantly inhibit the sSema4D-induced endothelial cell migration, and FH and FG were more effective in inhibiting endothelial cell migration than Sema4D neutralizing antibody (BMA-12).

2) The nano small peptides FH and FG significantly inhibit endothelial cell leakage.

A layer of fibronectin was first applied to coat the upper layer of a 24-well transwell chamber (0.4 um) and incubated at room temperature for 1 h; after coating, the mouse brain microvascular endothelial cells were seeded, and cultured for 5 days until the cells were full, and then FH (20 µM), FG (20 µM), and Sema4D neutralizing antibody (BMA-12) (2 µg/µL) were added to the medium (the concentration of sSema4D in the medium was 1600 ng/mL), respectively. An equal volume of DMSO was added as a control, and ECM was used as a blank control. After incubation for 36 h, the resistance value was measured by a cell transmembrane resistance measuring instrument.

Figure 6C:
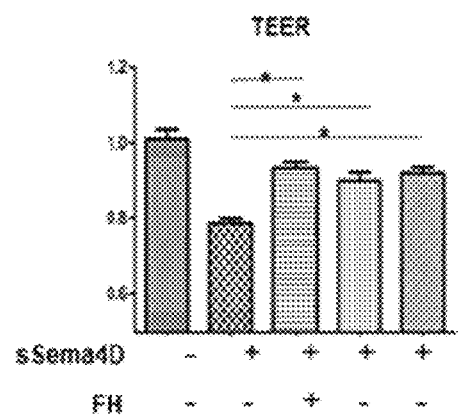

The results are shown in FIG. 6C: At 36 h, FH and FG can significantly inhibit sSema4D-induced endothelial cell leakage, and the effect of FH and FG was comparable to that of Sema4D neutralizing antibody (BMA-12).

Example 7

The nano small peptides FH and FG significantly inhibit pericyte migration (transwell experiment).

The primary mouse brain microvascular pericytes were starved with 0.5% PM for 4 to 6 h. The pericytes were seeded in the upper layer of a 24-well transwell chamber (8 µm). The medium containing FH (20 µM), FG (20 µM), and Sema4D neutralizing antibody (BMA-12) (2 µg/µL) (the concentration of sSema4D in the medium is 1600 ng/mL) was added to the lower chamber, and an equal volume of DMSO was added as control. The cells were incubated in a 5% CO2 incubator at 37° C. for 36 h. 36 h later, the cells on the bottom of the chamber were fixed with 4% paraformaldehyde and stained with crystal violet, and the pericytes that penetrated to the bottom of the chamber were counted under a microscope.

Figure 7A:
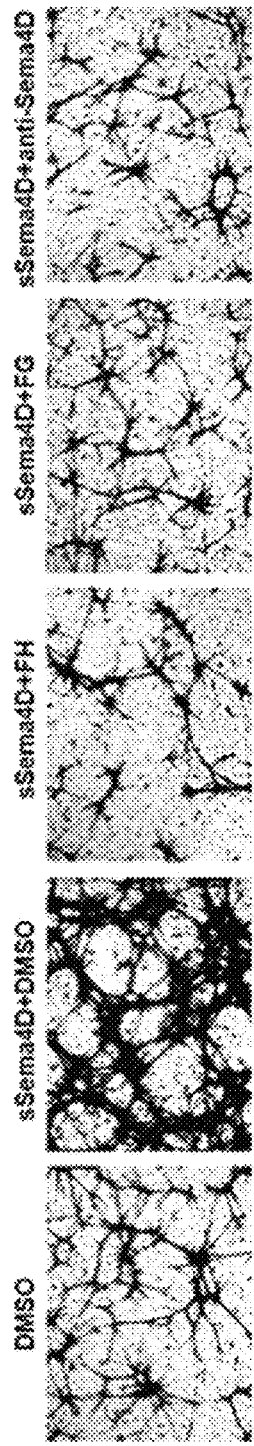
Figure 7B:
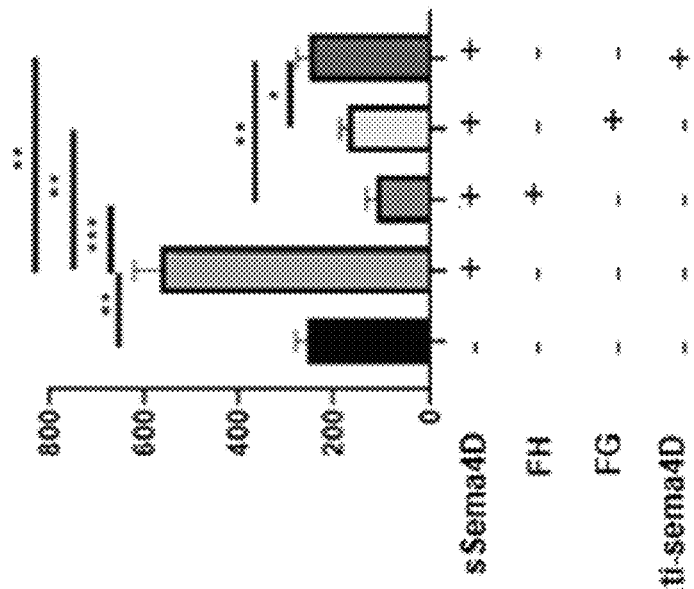

The results are shown in FIGS. 7A and 7B: At 36 h, FH and FG can significantly inhibit the sSema4D-induce pericyte migration, and FH was more effective in inhibiting pericyte migration than Sema4D neutralizing antibody (BMA-12).

Example 8

1) In vivo imaging of small animals confirmed that nano small peptides FH and FG entered the vitreous humor of mice in the form of eye drops and vitreous injection.

10 µL of FH and FG eye drops (with the concentration of 20 µM, the solvent therein was artificial tears) were instilled on the eyeball surface of mice (8-week-old C57 male mice), once at an interval of 1 h. One hour after the third eye drop, the mice were anesthetized to have cardiac perfusion, the eyeballs of the mice were taken out, the connective tissue on the eye surface was trimmed, and the eyeballs were washed with PBS solution for several times to remove the nano eye drops from the surface of the eyeballs. The eyeball was placed in a small animal imager (at emission wavelength of 535 nm and excitation wavelength of 490 nm) for image acquisition.

Mice (8-week-old C57 male mice) were anesthetized with 4.3% chloral hydrate (0.01 ml/g), and antibiotic eye drops (levofloxacin eye drops), ocular surface anesthetics (Obucaine hydrochloride eye drops) were instilled before the surgery. The head position of the mouse was adjusted to keep the eyeball at the level of the corneal limbus. A small incision was made 1 mm behind the corneal limbus with an insulin injection needle, and 1 µl of nanomedicine FH (20 µM, FG (20 µM) or solvent was injected into the vitreous cavity along the small incision with a Hamilton 33G syringe); the needle tip entered vertically and then tilted, and after pushing, the needle was retained for 0.5 to 1 min, and the needle was then pulled out quickly. Antibiotic eye drops were used for 3 days after the surgery to prevent infection.

Figures 8A, 8B:
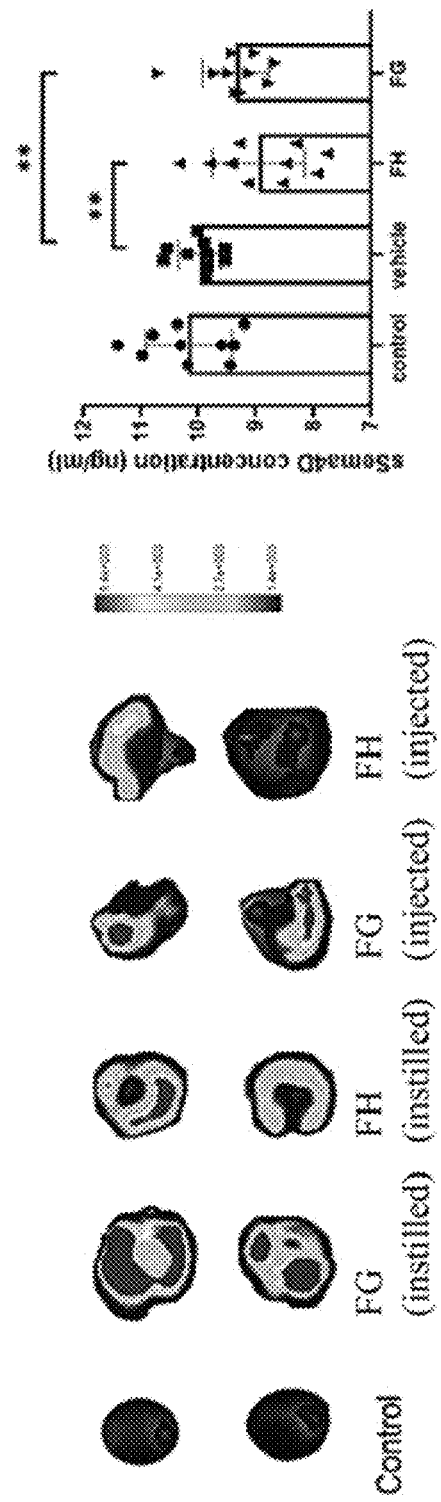

The results are shown in FIG. 8A.

2) Elisa tests show that FH and FG eye drops can reduce the concentration of sSema4D in vitreous humor.

In this example, 8-week-old C57 male mice were used, with ten data points in each group, and each data point was the average of the experimental results of 5 mice.

10 µL of 20 µM FH and FG eye drops (the solvent therein was artificial tears) were instilled on the surface of the mouse eyeball, once in the morning and once in the evening. After 3 days of eye instillation, the mice was anesthetized to have cardiac perfusion, then the mouse eyeball was taken out and then washed with PBS solution for several times to remove the nano eye drops from the surface of the eyeballs. The water on the eyeballs was then removed with filter paper to release and collect the vitreous humor. ELISA kit (Shanghai Yuanmu Biotechnology Co., Ltd.) was used to detect the expression of sSema4D protein in vitreous humor.

Control group was instilled with the same volume of PBS solution; vehicle group was instilled the same volume of artificial tears (Systane).

The results are shown in FIG. 8B. Both FH and FG can be prepared into drops and instilled in eyes to reduce the expression of sSema4D protein in the vitreous humor.

What is claimed is:

1. An artificially synthesized peptide having a molecular formula of X-FFVLKKNKAAKG (SEQ ID NO:1), wherein the X is dodecanoyl, tetradecanoyl, hexadecanoyl, or octadecanoyl group.

2. A method for treating fundus vascular disease in a subject in need thereof, wherein the method comprises
preparing a pharmaceutical composition comprising the peptide according to claim 1, and
administering the pharmaceutical composition to the subject.

3. The method according to claim 2, wherein the fundus vascular disease is caused by angiogenesis of fundus.

4. The method according to claim 2, wherein the fundus vascular disease is caused by pathological vascular leakage of the fundus.

5. The method according to claim 2, wherein the fundus vascular disease is caused by pericyte function change.

6. The method according to claim 2, wherein the fundus vascular disease is caused by endothelial cell migration or leakage.

7. The method according to claim 2, wherein the pharmaceutical composition is in the form of tablet, capsule, granule, form for injection, powder, or drop.

* * * * *

SEQUENCE LISTING

Sequence total quantity: 2
SEQ ID NO: 1          moltype = AA   length = 12

-continued

```
FEATURE                Location/Qualifiers
NON_TER                1
                       note = modified at N' terminal with dodecanoyl,
                        tetradecanoyl, hexadecanoyl, or octadecanoyl group.
source                 1..12
                       mol_type = protein
                       organism = synthetic construct
SEQUENCE: 1
FFVLKKNKAA KG                                                             12

SEQ ID NO: 2           moltype = AA  length = 12
FEATURE                Location/Qualifiers
NON_TER                1
                       note = modified at N' terminal with dodecanoyl,
                        tetradecanoyl, hexadecanoyl, or octadecanoyl group.
source                 1..12
                       mol_type = protein
                       organism = synthetic construct
SEQUENCE: 2
FFVLKKQKRP RH                                                             12
```